United States Patent
Kumar et al.

(10) Patent No.: US 7,531,190 B2
(45) Date of Patent: May 12, 2009

(54) POROUS CERAMIC STRUCTURE CONTAINING BIOLOGICS

(75) Inventors: Mukesh Kumar, Warsaw, IN (US); Elizabeth A Schlueter, Leesburg, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 378 days.

(21) Appl. No.: 11/137,346

(22) Filed: May 25, 2005

(65) Prior Publication Data

US 2006/0271201 A1    Nov. 30, 2006

(51) Int. Cl.
*A61K 9/00* (2006.01)
*A61F 2/00* (2006.01)

(52) U.S. Cl. .................... 424/423; 424/400; 424/422

(58) Field of Classification Search ........... 424/400, 424/405, 422, 423
See application file for complete search history.

(56) References Cited

U.S. PATENT DOCUMENTS

| | | | |
|---|---|---|---|
| 6,118,043 A | 9/2000 | Nies et al. | |
| 6,139,585 A | 10/2000 | Li | |
| 6,302,913 B1 | 10/2001 | Ripamonti et al. | |
| 6,451,059 B1 | 9/2002 | Janas et al. | |
| 6,508,838 B2 | 1/2003 | Lee et al. | |
| 6,719,989 B1 | 4/2004 | Matsushima et al. | |
| 6,746,488 B1 | 6/2004 | Bales | |
| 2001/0020188 A1 | 9/2001 | Sander | |
| 2001/0041942 A1 | 11/2001 | Ylanen et al. | |
| 2002/0128722 A1 | 9/2002 | Jefferies | |
| 2003/0004578 A1* | 1/2003 | Brown et al. | 623/23.72 |
| 2003/0028196 A1* | 2/2003 | Bonutti | 606/87 |
| 2003/0033021 A1 | 2/2003 | Plouhar et al. | |
| 2003/0033022 A1 | 2/2003 | Plouhar et al. | |
| 2004/0064194 A1 | 4/2004 | Irie et al. | |
| 2004/0153165 A1 | 8/2004 | Li et al. | |

FOREIGN PATENT DOCUMENTS

| | | |
|---|---|---|
| EP | 1270205 | 1/2003 |
| EP | 1277450 | 1/2003 |
| EP | 1374922 | 1/2004 |
| EP | 1410811 | 4/2004 |
| WO | WO-97/31661 | 9/1997 |
| WO | WO-01/82989 | 11/2001 |
| WO | WO-0211781 | 2/2002 |
| WO | WO-03026714 | 4/2003 |
| WO | WO-2004/101013 | 11/2004 |

* cited by examiner

*Primary Examiner*—Ruth A Davis
(74) *Attorney, Agent, or Firm*—Harness, Dickey

(57) ABSTRACT

A ceramic scaffold operable to support a defect in bone and a surrounding healthy tissue comprising a ceramic body having a plurality of pores, the pores having a bioactive material incorporated therein, wherein the bioactive material adheres to the ceramic body with a resorbable material adhesive. Methods of manufacture and methods of augment a bone defect site are also provided.

19 Claims, 3 Drawing Sheets

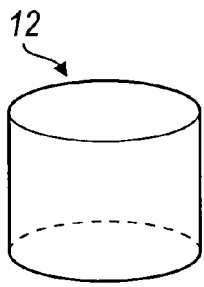
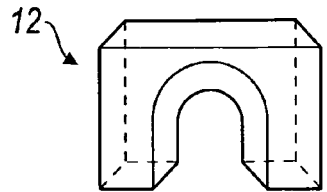
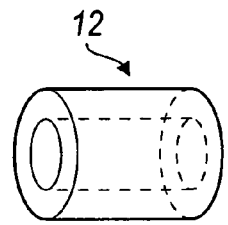
FIG. 5A    FIG. 5B    FIG. 5C
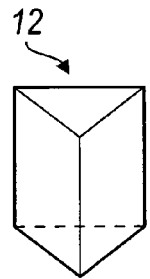
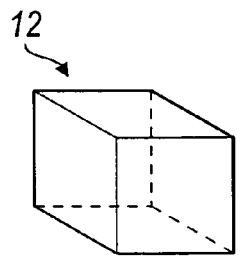
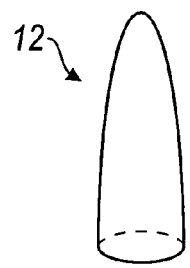
FIG. 5D    FIG. 5E    FIG. 5F
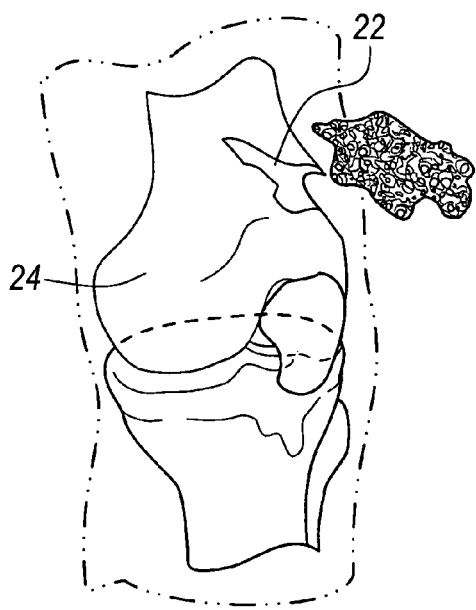
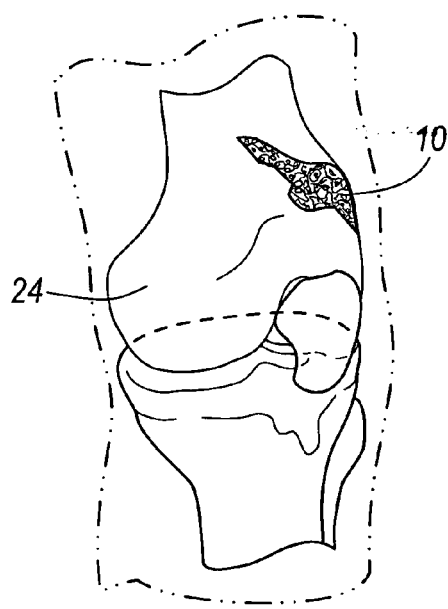
FIG. 6A    FIG. 6B

POROUS CERAMIC STRUCTURE CONTAINING BIOLOGICS

FIELD OF THE INVENTION

The present invention relates to porous ceramic structures containing bioactive materials. More particularly, the present invention relates to porous ceramics for use as a scaffold in orthopedic surgical procedures to repair bone defects.

BACKGROUND OF THE INVENTION

Osseus defects may be caused by trauma, pathological disease, surgical intervention, or other situations. Some defects may be minor and require minimal surgical intervention, such as filling the defect with a bone filler, or heal on their own with the support of a sling or splint. Some defects may be more severe, such as those located in critical load bearing regions of the bone. These defects may be of a large enough size to require internal support with a prosthetic device.

Prosthetic devices may be either non-resorbable or resorbable. Non-resorbable prosthetic devices may include biocompatible metals, ceramics, or composites. These devices may be designed to provide strength to the defect to withstand various compressive and other load forces. Some non-resorbable prosthetics may be designed with space to incorporate new bone ingrowth, but the nature of the non-resorbable materials prevents ingrowth because the materials are generally non-osteoinductive. Furthermore, the non-resorbable materials may be implanted to merely fill the defect site and do not wrap around the healthy tissues adjacent to the defect site where additional support may help expedite the healing process.

Resorbable structures actively induce the ingrowth of adjacent bone tissue through osteoinduction. Demineralized bone matrix is a resorbable material known to possess high osteoinductive potential. Although they encourage bone ingrowth, similar to the shortcomings of the non-resorbable materials, resorbable structures are generally placed into the defect site and not around the supporting healthy tissues. While it may be desirable to replace the resorbable structures with freshly generated tissues, resorption of the materials changes the shape of the implant, thereby altering its strength. As such, these implants may be preferred for use in non- or minimally load bearing areas of the body.

The non-resorbable or resorbable structure may be a porous structure incorporating a filling material. The filling materials may adhere to the porous structure with an adhesive such as a biological glue (fibrin or animal derived adhesive) or a chemical glue, such as cyanoacrylate. While the selection of adhesives may provide the desired retention of the filling material in the structure, it may be desirable to use an adhesive which further optimizes bone ingrowth.

Therefore, it may be desirable to provide an implant which provides structural integrity, induces bone ingrowth, and is advantageous for use throughout the body.

SUMMARY OF THE INVENTION

Embodiments of the present invention relate to ceramic scaffolds operable to support a defect in bone and a surrounding healthy tissue comprising a ceramic body having a plurality of pores, the pores having a bioactive material incorporated therein, wherein the bioactive material adheres to the ceramic body with a resorbable material adhesive. The ceramic body may be made, for example, of hydroxyapatite, tricalcium phosphate, biocompatible ceramics, calcium phosphates, and mixtures thereof. The ceramic body pores may be of different sizes and may be distributed through an entire region of the ceramic body including a surface on the body. The resorbable material adhesives may be a demineralized bone matrix, collagen, including natural collagen and modified collagen, naturally occurring tissue-derived proteins, natural polysaccharides, synthetic polysaccharides, and mixtures thereof. The ceramic body may also include bioactive materials selected from the group consisting of calcium containing materials, nutrient factors, bone morphogenic proteins, growth factors, antimicrobials, anti-inflammatory agents, blood products, and mixtures thereof. The ceramic scaffold may be osteoconductive and osteoinductive and may at least partially form around an internal structure.

Various embodiments of the present invention provide methods of preparing a ceramic scaffold, comprising: applying an adhesive layer to a region of a porous ceramic body, said adhesive layer comprising at least one of a demineralized bone matrix, collagen, including natural collagen and modified collagen, naturally occurring tissue-derived proteins, natural polysaccharides, synthetic polysaccharides, and mixtures thereof; drying the adhesive layer; and applying a second over-layer comprising a bioactive material to the adhesive layer. The adhesive layer and/or the over-layer may be applied using injection, submersion, capillary action, spraying, rolling, and mixtures thereof. The adhesive layer may be applied to a plurality of pore walls of the ceramic. The drying may be achieved by freeze drying, vacuum drying, air drying, temperature flux drying, and combinations thereof. A sterilization step, such as radiating the ceramic scaffold, may be performed. The over-layer may be of a thickness which is greater than the thickness of the adhesive layer. The over-layer may also at least partially permeate the adhesive layer.

Various embodiments of the invention provide methods of augmenting a site in need of repair, comprising providing a porous ceramic scaffold comprising a ceramic body having a plurality of pores, the pores having a resorbable material adhesive and a bioactive material incorporated therein, wherein the scaffold is operable to support a defect in bone and the surrounding healthy tissues; and placing the porous ceramic scaffold at the site in need of repair. Porous ceramic scaffolds may also be placed on the healthy bone and tissues adjacent to the defect region. The porous ceramic scaffold may be at least partially dehydrated. The dehydrated porous ceramic scaffold may be hydrated with water, saline, blood, bone marrow aspirates, derivatives thereof, and mixtures thereof.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 5A-5F depict shapes of porous ceramic scaffolds according to various embodiments;

FIGS. 6A-6B depict the repair of a knee defect with a porous ceramic scaffold according to various embodiments;

DETAILED DESCRIPTION OF THE PREFERRED EMBODIMENTS

The following description of the preferred embodiment(s) is merely exemplary in nature and is in no way intended to limit the invention, its application, or uses. Although various embodiments may be illustrated in conjunction with a knee or with a prosthetic hip implant, it is understood that the ceramic scaffold and methods of this invention may be of any appropriate shape and may be used with any appropriate procedure and not solely those illustrated.

As depicted in FIGS. 1-4, a porous ceramic scaffold 10 comprises a ceramic body 12 having a plurality of pores 14 having a bioactive material adhered to the ceramic body 12 with a resorbable material adhesive. The ceramic body 12 materials can include hydroxyapatite, tricalcium phosphate, biocompatible ceramics, calcium phosphates and mixtures thereof. The ceramic scaffold 10 is operable to support a defect in bone and a surrounding healthy tissue.

The ceramic body 12 may be of any general shape as depicted in FIGS. 1-4 and 5A-5F. Ceramic body 12 types may include circles, ellipses or polygons such as triangles, tetragons, pentagons, hexagons, heptagons, octagons, ennagons, decagons, hendecagons, dodecagons, the n-gons (polygons with greater than thirteen sides) and etc. The ceramic body 12 may be a cyclic polygon such that all vertices lie within a sphere or it may have an irregular shape. The ceramic body 12 may be a circle, oval, curve, free-form or other non-polygon shape. It is generally desirable to have the shape of the ceramic body 12 facilitate use with a site in need of bone repair or any instruments used in conjunction with the bone repair or with the ceramic scaffold 10 (i.e.: diameter of the instrument openings and a femoral implant, for example, in hip arthroplasty). The shapes may be substantially solid bodies such as a cylinder or block, or the shapes may include contoured regions such as horse-shoe, disk, or tube. The ceramic body 12 may be designed to have protrusions which wrap around internal structures, such as bones, or the body shape may conform to the internal structure, as seen in FIG. 6B, for example.

The ceramic body 12 may also be shaped for easy use and manipulation. Any initial ceramic body 12 shape may be split to create any final shape of a reduced size. If the desired body 12 for implantation was a 5 centimeter squared cube, a 10 centimeter by 5 centimeter rectangular block could be split in half to provide the cube or the rectangular block could be fragmented to provide a plurality of free form pieces. The breaking may be achieved by hand manipulation or using a tool such as a hammer or chisel. The initial larger ceramic body 12 may be scored for example to include break lines to facilitate creating several pieces from a larger ceramic body 12.

Figure 1:
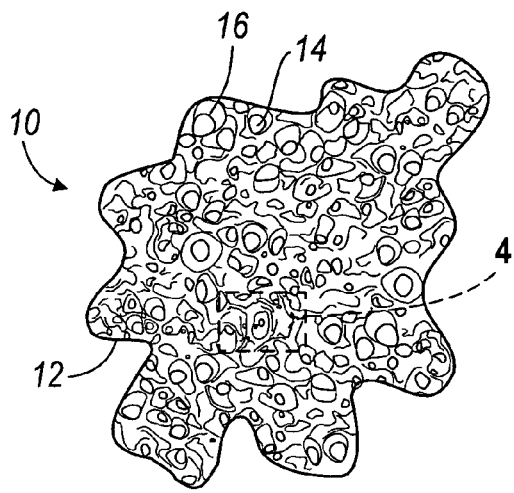
FIG. 1 depicts a porous ceramic scaffold according to various embodiments.
Figure 4:
FIG. 4 depicts an exploded view of a porous ceramic scaffold according to various embodiments.
Figure 2:
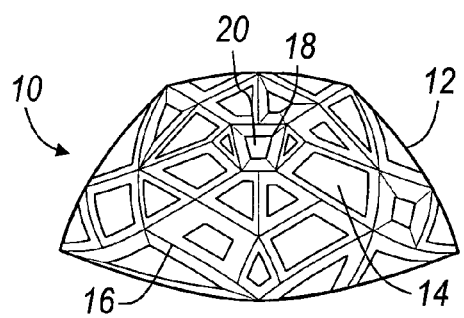
FIG. 2 depicts a porous ceramic scaffold according to various embodiments.
Figure 3:
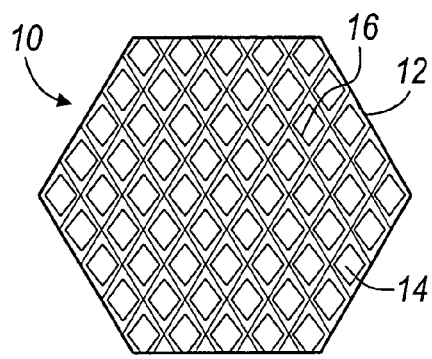
FIG. 3 depicts a porous ceramic scaffold according to various embodiments.
Figure 7A:
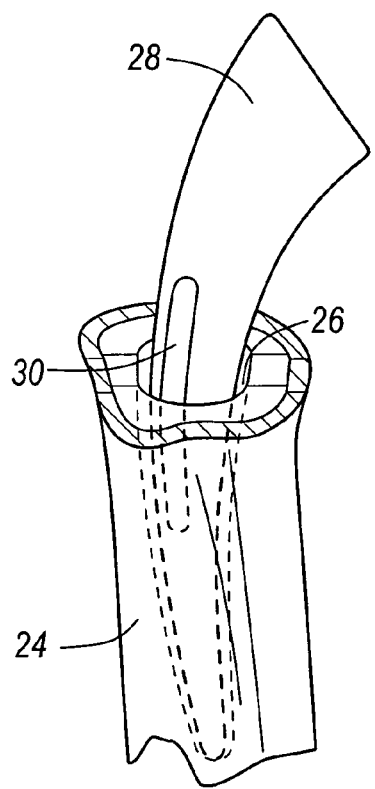
FIGS. 7A-7B depict use of a porous ceramic scaffold with a femoral stem implant according to various embodiments.
Figure 7B:
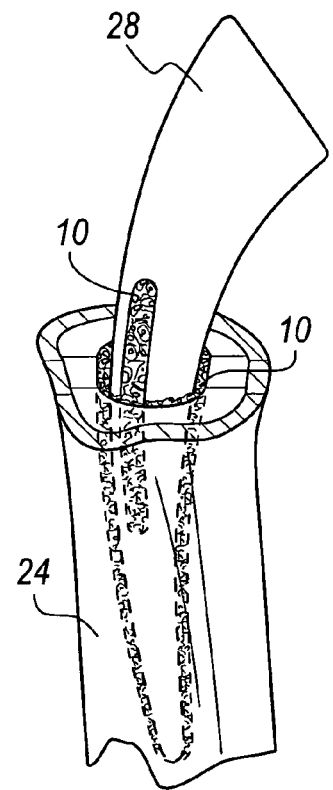
Figure 8A:
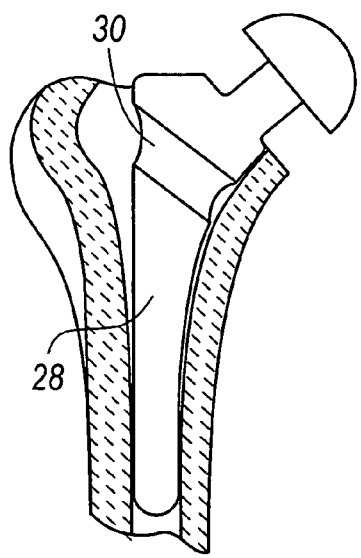
FIGS. 8A-8B depict use of a porous ceramic scaffold with a prosthetic hip according to various embodiments.
Figure 8B:
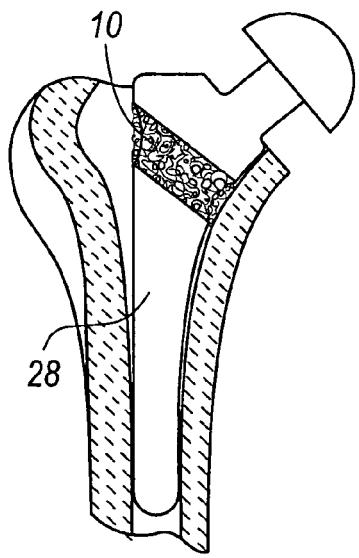

Returning to FIGS. 1-4, the pores 14 create a volume void in the ceramic body 12. Pores 14 are defined by the pore walls or internal surfaces 16 of the ceramic body 12. Pores 14 are generally of a selected depth and width and may be of a uniform size, a collection of different sizes, or randomly sized. For example, the ceramic body 12 as depicted in FIG. 3 may be limited to pores 14 of one size, while another ceramic body 12, for example, as best depicted in FIG. 4, may comprise a collection of randomly sized and distributed pores 14. The pores 14 may partially transverse the ceramic body 12, may be distributed through an entire region of the ceramic body 12 including a surface thereof, or the pores 14 may be entirely contained in the ceramic body 12. The pores 14 may be open to one another to form a continuous flow path or channels throughout the ceramic body 12. In one embodiment, the ceramic body 12 may be sponge-like, comprising a plurality of different sized pores 14 which may or may not be continuous, and/or interconnected. The ceramic body 12 may be of high porosity having from about 70% to about 90% pore volume or of a lesser porosity, having from about 25% to about 70% pore volume. It is understood that the size of pores 14 may be altered by one skilled in the art based on the ceramic scaffold 10 dimensions, desired end weight, desired porosity, and intended usage.

The combination of porosity, pore 14 shape, and materials used may impact the structural integrity of the ceramic scaffold 10. By selecting the proper materials and porosity, the ceramic body 12 having empty pores 14 and the ceramic scaffold 10 having the filled pores 14 may provide equivalent load bearing capabilities. This is particularly beneficial when using resorbable materials because throughout the compositional changes of the ceramic scaffold 10, structural integrity and support are not compromised.

The pores 14 of the ceramic scaffold 10 have a resorbable material adhesive incorporated therein. The resorbable materials may encourage bone growth into the ceramic scaffold 10 more than other adhesives, such as chemical adhesives. Resorbable materials may include demineralized bone matrix, collagen, naturally occurring tissue-derived proteins, including without limitation such as elastin, silk, fibrin, fibrinogen, etc., natural polysaccharides, including without limitation hyaluronic acid, chitin, chitosan, alginate, carboxymethylcellulose, other polysaccharides, and various mixtures thereof. While certain examples may include demineralized bone matrix or collagen, it is understood that any of the aforementioned resorbable materials may be used in embodiments of the present invention. The resorbable material adhesive may be wet when applied to the ceramic body 12, as discussed later herein, and subsequently dried.

Demineralized bone matrix may include bone from a single member of the same species as the patient to reduce or prevent an immunogenic response or the bone may come from multiple donors. The demineralized bone matrix may be from a cortical, cancellous and/or corticocancellous bone. As used herein, the term "demineralized" and variants thereof, means a loss or decrease of the mineral constituents or mineral salts of the individual tissues or bone relative to their natural state. The demineralized bone may have a calcium concentration of about 1%. The demineralized bone may be dried to a final moisture level of about less than 6% as recommended by the American Association of Tissue Banks. The demineralized bone material is of sufficient size to fit into the pores 14.

Collagen materials may be natural or modified. Natural collagen materials may include nonhydrolyzed native proteins derived from the connective tissue of lower animals, humans, fish, and any other living being which produces collagen. Modified collagen may be hydrolyzed collagen which is the hydrolysate of animal or fish collagen derived by acid, enzyme, or another suitable means of hydrolysis. The relative amounts of the demineralized bone material, collagen or mixtures thereof may be up to 90% of the final weight of the ceramic scaffold 10. It is understood that the amounts of each component used may vary.

The ceramic scaffold 10 also includes a bioactive material. Bioactive materials include, but are not limited to, calcium containing materials, nutrient factors, bone morphogenic proteins, growth factors, antimicrobials, anti-inflammatory agents, blood products, and mixtures thereof. (For additional examples, see U.S. Pat. No. 6,180,606, Chen, et al., issued Jan. 30, 2001, incorporated by reference.) Depending on the bioactive material(s) selected, the ceramic scaffold 10 may be osteogenic and osteoinductive. The bone building materials may be contained in the pores 14 of the ceramic scaffold 10 or the ceramic body 12 or coated onto the outer surface of the ceramic scaffold 10 or the ceramic body 12.

"Calcium containing" materials include, but are not limited to, hydroxyapatite, monobasic, dibasic and tribasic calcium phosphates, calcium aluminates, calcium containing ceramics, porous calcium containing ceramic particles, and amorphous calcium phosphate.

A "nutrient factor" can include a compound or series of compounds used to sustain metabolic activities or used to promote normal physiologic function or optimal health. Nutrient factors include, but are not limited to, vitamins, hormones, individual or combinations of amino acids, carbohydrates or derivatives thereof, fats or derivatives thereof, alcohols or derivatives thereof, inorganic salts, and trace elements.

A "Bone Morphogenic Protein" can include any of the zinc metalloendopeptidase enzymes involved in induction of bone and cartilage formation. Bone Morphgenic Proteins include Bone Morphogenic Protein-2 (BMP-2), Bone Morphogenic Protein-2a (BMP-2a), Bone Morphogenic Protein-4 (BMP-4), Bone Morphogenic Protein-5 (BMP-5), Bone Morphogenic Protein-6 (BMP-6), Bone Morphogenic Protein-7 (BMP-7), and Bone Morphogenic Protein-8 (BMP-8).

A "growth factor" can include a substance that is operable to increase the size of a living being or any of its parts or to stimulate cell growth. Growth factors include Transforming Growth Factor-beta (TGF-β), Transforming Growth Factor-alpha (TGF-∝), Epidermal Growth Factor (EGF), Insulin-like Growth Factor-I or II, Interleukin-I, Interferon, Tumor Necrosis Factor, Fibroblast Growth Factor (FGF), Platelet Derived Growth Factor (PDGF), and Nerve Growth Factor (NGF).

An "anti-inflammatory" can include an agent that reduces inflammation without directly antagonizing the causative agent. "Anti-inflammatories" include, but are not limited to, steroidal agents such as flucinolone and hydrocortisone, and nonsteroidal agents (NSAIDs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone and phenylbutazone.

A "blood product" can include a product, any component of which is derived from blood. Blood products include, but are not limited to, whole blood and blood fractions, such as plasma, blood cells, blood factors, blood related proteins, unspecialized cells such as stem cells (including adipose derived stem cells), or specialized cells, e.g., types of leukocytes such as lymphocytes and dendritic cells.

Other suitable bioactive materials may include inorganic materials, osteoblasts, amino acids, gelatin, additional collagen, naturally occurring or synthetic therapeutic drugs, proteins, enzymes, and mixtures thereof.

The present invention also provides methods of preparing the ceramic scaffold 10. Referring to FIG. 2, an adhesive layer 18 comprising a resorbable material selected is applied to a region of the porous ceramic body 12. The adhesive layer 18 may be applied to all of the pore internal surfaces 16 or the adhesive layer 18 may be selectively applied to pores 14. For example, it may be desirable to coat some of the pores 14 with a demineralized bone matrix adhesive layer 18 and the remainder of the pores 14 with collagen adhesive layer 18.

Applying the adhesive layer 18 to the ceramic body 12 may be performed with any suitable technique, including, but not limited to, using a syringe to inject the material into the pores 14, submerging the ceramic body 12 into the material for uptake, through the use of capillary action, spraying, rolling, and mixtures thereof. Depending on the desired thickness of the adhesive layer 18, a single technique or a combination of techniques may be employed. For example, when applying an ultra thin adhesive layer 18 (from about 10 nm to about 5 mm) a spray type application utilizing a fine mist may provide greater control. When a thicker adhesive layer 18 is preferred, rolling or submerging the ceramic body in the adhesive layer 18 material may provide a thick layer more quickly than other techniques.

The adhesive layer 18 may then be dried onto the ceramic body 12. The drying occurs at a temperature and for a duration sufficient to provide secure attachment of the adhesive layer 18 to the ceramic body 12. The application of any heat, light, or air drying methods must be performed in a manner such that the structural integrity of the ceramic scaffold 10 and the benefits derived from the inclusion of various bioactive materials is not compromised. For example, in an embodiment where the bioactive material comprises a protein, the drying temperature should not reach a temperature at which the protein would be significantly denatured and/or lose functionality.

A second over-layer 20 comprising a bioactive, may be applied to the adhesive layer 18. The second over-layer 20 may be applied to discrete internal surfaces 16 or all of the pore internal surfaces 16. The second over-layer 20 may be of a smaller, greater, or the same thickness as the adhesive layer 18. An interaction may occur between the second over-layer 20 and the adhesive layer 18 such that at least some of the over-layer 20 permeates into the adhesive layer 18.

Additionally, several second over-layers 20 may be used. For example, a vitamin layer, a platelet concentrate layer, and a growth factor layer may all be applied over a single adhesive layer 18, such as demineralized bone matrix. In such an embodiment, the plurality of second over-layers 20 may also include an additional adhesive layer 18 between selected or each adhesive layer 18. Drying steps may be employed between the application of each or selected layers. Additionally, the ceramic scaffold 10 may be sterilized, such as by radiating the ceramic scaffold 10.

Referring to FIGS. 6A-6B, 7A-7B and 8A-B, embodiments of this invention may be used to repair bone defects. As used herein, "bone defects" or "injury sites," and variants thereof, can include bone imperfections caused by birth defect, trauma, disease, decay or surgical intervention, and the desired repair may be for cosmetic or therapeutic reasons.

Although the bone defects are depicted as knee and hip related defects, the methods and materials may be used for any defect. Embodiments of the ceramic scaffold 10 may be used to correct bone defects in orthopedic, neurosurgical plastic or reconstructive surgery, in periodontal procedures, and in endodontic procedures. Examples include repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g. deficit filling, discectomy, laminectomy, excision of spinal cord tumors, anterial cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, sinus lifts, etc. The standard surgical and dental procedures are suitable for use with the various methods. (See, e.g., U.S. Pat. No. 6,180,606, Chen, et al., issued Jan. 30, 2001 and U.S. Pat. No. 5,507,813, Dowd, et al., issued Apr. 16, 1996.)

Various embodiments of the present invention provide methods of augmenting a site in need of repair 22, comprising providing a porous ceramic scaffold 10 comprising a ceramic body 12 having a plurality of pores 14, the pores 14 having a resorbable material adhesive and a bioactive incorporated therein, where the scaffold is operable to support a bone defect and a surrounding tissue; and placing the porous ceramic scaffold 10 at the site in need of bone repair 22. The ceramic scaffold 10 may be placed into the defect site 22 with a surgical tool or with the surgeon's hands.

In embodiments where the ceramic scaffold 10 is smaller than the defect site 22, the surgeon may place a single ceramic scaffold 10 or several ceramic scaffolds 10 in the defect site 22 and manipulate them appropriately by hand or with a surgical tool. When the ceramic scaffold 10 is designed to fill and partially wrap around a defect site 22, the surgeon may match the contour of the ceramic scaffold 10 with the contour of the injury site 22 and insert the ceramic scaffold 10 into the void. In an embodiment where several ceramic scaffold(s) 10 are used to provide strength of an injury site 22, the ceramic scaffolds 10 may be oriented to maximize strength of the repair. For example, a first ceramic scaffold 10 may wrap around the left-most and right-most edges of the defect site 22 and surrounding healthy tissues to provide lateral support while another ceramic scaffold 10 may be arranged in the same defect site 22 and surrounding healthy tissues to provide vertical support.

As depicted in FIGS. 6A and 6B, the ceramic scaffold 10 may be used to augment the defect site 22 in the femur 24 above the patella. Because this region of the femur 24 is subject to high load and stress, the ceramic scaffold 10 is placed into the defect site 22 to provide supplemental strength. Regenerated tissue will grow into the ceramic scaffold 10 and replace the demineralized bone matrix, collagen and/or bioactive materials in the pores 14.

Referring to FIGS. 7A and 7B and 8A and 8B, the ceramic scaffold 10 may also be used to augment defect sites 22 resultant from surgical intervention. Using the ceramic scaffold 10 in conjunction with a prosthetic device may improve stability and longevity of the device by incorporating the patient's natural bone as a means for support. For example, in hip arthroplasty, it may be necessary to prepare a tunnel 26, or surgically induced defect site 22, within the femur 24 to provide space for the femoral stem implant 28. The femoral stem implant 28 may be secured in the tunnel 26 with a surgical fixative, but a ceramic scaffold 10 may be used to provide the proper fit between the tunnel 26 and the femoral stem implant 28. The femoral stem implant 28 may also include recessed regions 30 into which the ceramic scaffold 10 may be placed. This ceramic scaffold 10 fits into and around the femoral stem implant 28 and also abuts the bone tunnel 26 and provides enhanced strength to the region upon ingrowth of regenerated bone.

In an embodiment where the ceramic scaffold 10 is substantially or completely dried, the ceramic scaffold 10 may be reconstituted or hydrated. The solution used to hydrate the ceramic scaffold 10 may include, but is not limited to, water, saline, blood, bone marrow aspirates, derivatives thereof, and mixtures thereof. In one embodiment, adding water to the dried bone may be achieved by adding blood to the ceramic scaffold 10. "Blood" includes, but is not limited to, whole blood and blood components such as, red blood cells and components, white blood cells and components, plasma, plasma fractions, plasma serum, platelet concentrate, blood proteins, thrombin, and coagulation factors.

The ceramic scaffold 10 may hydrate while in the defect site 22. Ambient fluids such as blood are absorbed after a few minutes. Extra corpus fluids, including but not limited to, saline, water or a balanced salt solution (140 mm NaCl, 5.4 mm KCl, pH 7.6) may be used to expedite the hydration. Hydration may also occur away from the defect site using the subject's blood or extra corpus fluids.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A ceramic scaffold operable to support a defect in bone and a surrounding healthy tissue comprising:
   a ceramic body defining a plurality of pores and having a resorbable material adhesive within said plurality of pores, said plurality of pores having at least two bioactive materials incorporated therein,
   wherein a first bioactive material is provided as a first layer atop said resorbable material adhesive and a second bioactive material is provided as a second layer atop said first layer within said pores of said ceramic material, and further wherein said first bioactive material adheres to said pores of said ceramic body by said resorbable material adhesive.

2. The ceramic scaffold according to claim 1, wherein said ceramic body is selected from the group consisting of hydroxyapatite, tricalcium phosphate, biocompatible ceramics, calcium phosphates, and mixtures thereof.

3. The ceramic scaffold, according to claim 1, wherein at least two of said pores are of different sizes.

4. The ceramic scaffold, according to claim 1, wherein at least one of said pores is distributed through an entire region of said ceramic body including a surface thereof.

5. The ceramic scaffold, according to claim 1, wherein said resorbable material adhesive is selected from demineralized bone matrix, collagen, naturally occurring tissue-derived proteins, natural polysaccharides, synthetic polysaccharides, and mixtures thereof.

6. The ceramic scaffold, according to claim 1, wherein said bioactive material is selected from the group consisting of calcium containing materials, nutrient factors, bone morphogenic proteins, growth factors, antimicrobials, anti-inflammatory agents, blood products, and mixtures thereof.

7. The ceramic scaffold, according to claim 1, wherein said scaffold is at least partially formed around an internal structure and a prosthetic device.

8. The ceramic scaffold, according to claim 1, wherein said ceramic scaffold is osteoconductive and osteoinductive.

9. The ceramic scaffold according to claim 1, wherein said bioactive material adheres to said ceramic body by permeating a region of the resorbable material adhesive.

10. The ceramic scaffold according to claim 1, wherein said adhesive layer has a first thickness and said bioactive layer has a second thickness which is greater than said first thickness.

11. The ceramic scaffold according to claim 1, wherein said ceramic scaffold is load-bearing.

12. The ceramic scaffold according to claim 1, wherein said ceramic scaffold is of a shape selected from the group consisting of: a cylinder, a block, a horse shoe, a disc, or a tube.

13. A ceramic scaffold operable to support a defect in bone and a surrounding healthy tissue comprising:
- a ceramic body defining a plurality of pores and having a resorbable material adhesive having a thickness of from about 10 nm to about 5 mm within said plurality of pores, said plurality of pores having at least two bioactive materials incorporated therein,
- wherein a first bioactive material is provided as a first layer atop said resorbable material adhesive and a second bioactive material is provided as a second layer atop said first layer within said pores of said ceramic material, and further wherein said first bioactive material adheres to said pores of said ceramic body by said resorbable material adhesive.

14. A ceramic scaffold operable to support a defect in a bone and at least partially form around an internal structure of the bone and a prosthetic device comprising:
- a. a ceramic body defining a plurality of pores;
- b. a resorbable adhesive comprising demineralized bone matrix coating said plurality of pores;
- c. at least one bioactive material coated over said demineralized bone matrix adhesive; and
- d. the prosthetic device defining at least one recessed region in which the ceramic scaffold is positioned.

15. The ceramic scaffold according to claim 14, wherein the prosthetic device comprises a femoral stem.

16. The ceramic scaffold according to claim 14, wherein at least two of said pores are of different sizes.

17. The ceramic scaffold according to claim 14, wherein said ceramic body is selected from the group consisting of hydroxyapatite, tricalcium phosphate, biocompatible ceramics, calcium phosphates, and mixtures thereof.

18. A ceramic scaffold operable to support a defect in bone and a surrounding healthy tissue comprising:
- a. a ceramic body comprising hydroxyapatite and defining a plurality of pores;
- b. a resorbable adhesive comprising demineralized bone matrix coating said plurality of pores and having a thickness of from about 10 nm to about 5 mm;
- c. a platelet concentrate layer over said resorbable adhesive; and
- d. at least one bioactive material selected from the group consisting of calcium containing materials, nutrient factors, bone morphogenic proteins, growth factors, antimicrobials, anti-inflammatory agents, blood products, and mixtures thereof,
- wherein said ceramic scaffold is sized to fit within an interior region of the bone defect and contoured to overlap the surrounding healthy tissue.

19. The ceramic scaffold of claim 18, wherein the ceramic scaffold is sized to fit within a recessed region of a femoral stem implant.

* * * * *